United States Patent [19]

Tasca

[11] Patent Number: 5,172,058
[45] Date of Patent: Dec. 15, 1992

[54] NON-DESTRUCTIVE EDDY CURRENT TESTING DEVICE WITH SIGNAL COMPENSATION FOR SIGNAL PROPAGATION DELAY

[75] Inventor: Jean-Pierre Tasca, Sainte Genevieve Des Bois, France

[73] Assignee: Compagnie Generale d'Automatisme CGA-HBS, Bretigny Sur Orge, France

[21] Appl. No.: 805,946

[22] Filed: Dec. 12, 1991

[30] Foreign Application Priority Data

Dec. 28, 1990 [FR] France ................. 90 16470

[51] Int. Cl.⁵ .................. G01N 27/90; G01R 33/12
[52] U.S. Cl. .................. 324/225; 324/232; 324/233; 324/238
[58] Field of Search ........... 324/225, 232, 233, 234, 324/238

[56] References Cited

U.S. PATENT DOCUMENTS

| | | | |
|---|---|---|---|
| 3,443,212 | 5/1969 | Renken | 324/240 |
| 4,059,795 | 11/1977 | Mordwinken | 324/233 |
| 4,084,136 | 4/1978 | Libby et al. | 324/238 |
| 4,230,987 | 10/1980 | Mordwinken | 324/233 X |
| 4,424,486 | 1/1984 | Denton et al. | 324/233 X |

FOREIGN PATENT DOCUMENTS 0033802  8/1981  European Pat. Off. .

OTHER PUBLICATIONS

WPIL/DERWENT, accession No. 89-363176 [49], Derwent Publications Ltd., Londres, GB; & SU-A-1 464 067 (V. I. Krapivin).
Patent Abstracts of Japan, vol. 9, No. 127 (P-360)[1850], May 31, 1985; & JP-A-60 11 158 (Nippon Kokan), Jan. 21, 1985.
WPIL/DERWENT, accession No. 85-036559 [06], Derwent Publications Ltd., Londres, GB; & SU-A-1 099 269 (V. I. Redko).

Primary Examiner—Gerard R. Strecker
Attorney, Agent, or Firm—Sughrue, Mion, Zinn, Macpeak & Seas

[57] ABSTRACT

An embodiment comprises a generator constituted by a quartz crystal oscillator and programmable frequency dividers; a power amplifier providing a periodic excitation signal, of squarewave form; two coils electromagnetically coupled to a metal part to be tested; and measuring means comprising two synchronous detectors for measuring the real part and the imaginary part of the difference between the complex impedances of the coils. The frequency stability of the generator effects an improvement in the accuracy of the impedance measurements, when these measurements are made at different frequencies. For application to non-destructive testing of metal parts by eddy currents, at different frequencies.

1 Claim, 2 Drawing Sheets

NON-DESTRUCTIVE EDDY CURRENT TESTING DEVICE WITH SIGNAL COMPENSATION FOR SIGNAL PROPAGATION DELAY

This invention relates to a non-destructive eddy current testing device. Such a device can be used, for example, to detect defects or inclusions of foreign materials or variations in composition in a metal part. It uses a method consisting in generating eddy currents at a location in the test piece by submitting this location to an alternating magnetic field and in detecting variation in these eddy currents, relative to a reference, by detecting a change in the impedance of at least one coil used to generate the eddy currents.

BACKGROUND OF THE INVENTION

A first known method consists in generating eddy currents by means of a single coil carrying an alternating current, measuring the impedance of this coil and comparing it with a reference impedance value determined from a part considered to be good. This method suffers from the difficulties of requiring a preliminary determination of a reference impedance and of yielding a result which depends on the temperatures of the part and the coil.

A second known method is a differential method overcoming these difficulties. It consists in generating eddy currents in two adjacent locations in the same part, by means of two identical coils carrying the same current, one in phase, one antiphase, and in measuring the difference between the impedances of these two coils. This difference is zero when the two locations of the test piece have the same composition, independently of variation in temperature and without preliminary calibration. The difference in impedance is not zero if the composition of the part is not identical at the two locations where the coils are disposed.

These non-destructive test methods allow testing to a depth of less than or equal to 1 cm. This is a function of the frequency of the alternating current passing through the coil or coils. This frequency is at present between 10 Hz and 5 MHz. In order to discriminate small differences in the composition of a material, it is known to effect several measurements of impedance or differences between impedances at different frequencies. Each set of values thus obtained constitutes a signature of the slight difference in composition. A part is judged good or bad by comparing its signature with a reference signature.

A conventional non-destructive eddy current testing device comprises a Wien bridge generator providing a sinusoidal signal; a power amplifier receiving and linearly amplifying this sinusoidal signal to provide a power excitation signal; two coils connected by cables to the output of the power amplifier so as to be fed with the power excitation signal inphase or antiphase, depending on the sense of connection of the coils, which are electromagnetically coupled to the test piece; measuring means for detecting variation in the impedance of a coil; and digital processing means adapted in particular to store the results of the tests.

The excitation current passing through the coils is sinusoidal because the impedance of a coil is a magnitude which is only defined for a given frequency and because an impedance is measured conventionally by subjecting it to a sinusoidal current. Moreover a sinusoidal current has the advantage that it is not distorted by propagation along a cable of great length. In fact it is necessary in some applications to connect the coils to the control device by cables of great length, up to two hundred meters. It is well known that a line of great length has a dispersive action on the different frequencies making up a signal propagating on the line. A non-sinusoidal signal is thus distorted, in a manner which is a function of the characteristics of the line. This distortion of non-sinusoidal signals compromises the accuracy of the measurements of impedance or the difference between impedances, because the measuring method requires a sinusoidal signal with low distortion. The conventional solution thus consists in using a sinusoidal signal generator.

The generator itself should have a very low distortion so as not to compromise the accuracy of measurements. For improved measuring accuracy, it should also have excellent frequency stability, because any fluctuation in the frequency degrades the signal-to-noise ratio of the measurement and thus degrades its accuracy. This degradation hinders the detection of small defects in a part.

The generator used conventionally to provide a signal of given frequency is a Wien bridge oscillator, because it has adequate frequency stability and low distortion. Unfortunately a Wien bridge oscillator does not exhibit these qualities when its frequency is varied, which makes it difficult to implement a variable frequency generator and reduces the accuracy of the measurements.

It is known to implement the measuring means with two synchronous detectors. In this case the accuracy of the measurement is reduced if the length of the cables is great. Thus the excitation signal takes a certain time to reach the coils and the measurement signal takes the same time to reach the synchronous detectors from the coils. Means are associated with the Wien bridge to provide the two synchronous detectors with respective sinusoidal reference signals of the same frequency as the excitation signal and in quadrature. These means are conventionally located near to the synchronous detectors, whereby the reference signals are phase-advanced relative to the measurement signal and the synchronous detectors function under non-optimal conditions. This phase advance is a function of the length of the cables and thus varies, depending on the circumstances of use of the control device; it is difficult to compensate since it is variable and it is necessary to act on an analog signal.

The object of the invention is to provide a non-destructive eddy current testing device which allows the frequency to be varied over a large range while obtaining an accuracy of measurement at least as great as that obtained at a fixed frequency with a Wien bridge oscillator, and which avoids accuracy being reduced on account of the use of cables of great length.

SUMMARY OF THE INVENTION

The invention provides a non-destructive eddy current testing device comprising:
  means for providing a periodic power excitation signal;
  at least one coil connected by a cable to an output of the means for providing the periodic power excitation signal and electromagnetically coupled to a test piece; and
  measuring means for detecting a change in the impedance of a coil;

wherein the means for providing a periodic power excitation signal comprise:
- a quartz crystal stabilized oscillator providing a pulsed signal at a constant frequency constituting a clock signal; and
- at least one programmable frequency divider for providing a periodic signal having a variable frequency which is a submultiple of that of the clock signal.

Such a device allows a variable frequency to be obtained over a very large range with very high stability and good resolution, since the stability of a quartz crystal oscillator is excellent and the resolution is determined by the number of stages provided in the frequency divider. By increasing the frequency of the quartz crystal oscillator and the number of stages, the interval between two consecutive values of frequency can be made as small as desired. The stability of a conventional quartz crystal oscillator is quite good enough, without any special precautions, to eliminate any loss of measuring accuracy caused by frequency instability.

The device also has the advantage of being easy to control by a digital processor, since a programmable frequency divider can be controlled by a binary word defining the frequency division ratio.

According to a further feature, the periodic power excitation signal is a periodic pulse signal with a mark-space ratio of 1:1, commonly called a squarewave, and the measuring means comprise means for filtering the fundamental frequency of the periodic power excitation signal.

Such a device has the advantage of simplifying the implementation of a control device comprising an oscillator stabilized by a quartz crystal, since it does not have to convert a pulse signal to a sinusoidal signal with low distortion.

A testing device in which the measuring means comprise at least one synchronous detector and in which the means for providing a periodic power excitation signal comprise means for providing each synchronous detector with a reference signal may include the improvement whereby, in order to compensate for the effect of the length of the cable, the means for providing a reference signal further comprise:
- means for measuring the propagation time of a signal passing from the means for providing a reference signal to a coil and back again; and
- means for imposing on each reference signal a delay equal to the propagation time thus measured.

Such a device thus allows the coil or coils to be located remote from the remainder of the control device, without the length of the cables causing a significant degradation in the accuracy of the measurement as would otherwise result from the signal returning from the coils being late relative to the signal provided as a reference to the synchronous detectors. It is particularly simple to implement because it is easier to shift automatically the phase of a pulse signal provided by frequency dividers, then the phase of an analog signal provided by a Wien bridge.

BRIEF DESCRIPTION OF THE DRAWINGS

An embodiment of the invention is described by way of example with reference to the accompanying drawings, in which.

DETAILED DESCRIPTION

Figure 1:
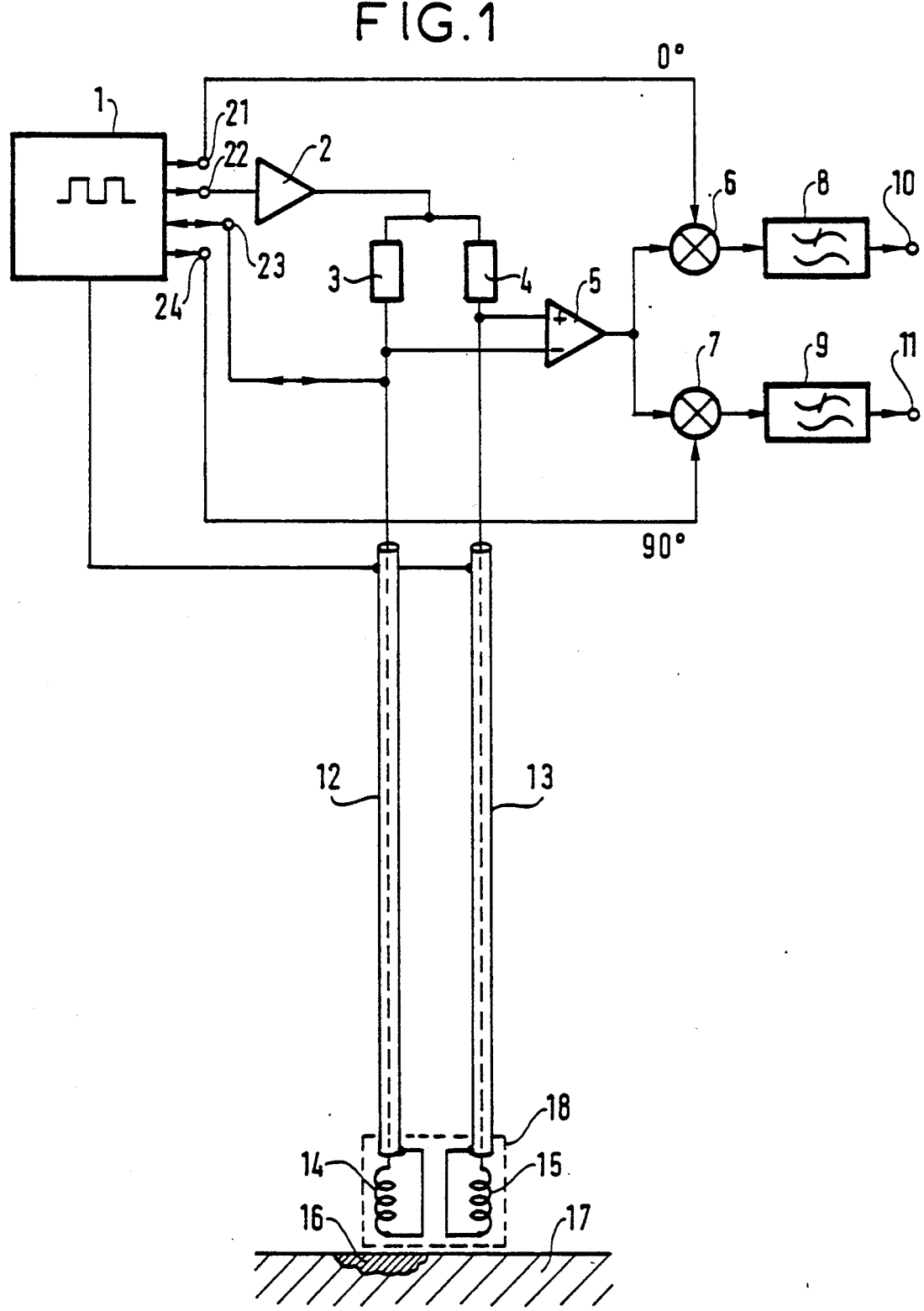
FIG. 1 is a general circuit diagram of an embodiment of the control device according to the invention.

In FIG. 1 the example shown comprises: a signal generator 1; a power amplifier 2; two identical impedances 3 and 4; a differential amplifier 5; a first synchronous detector formed by an analog multiplier 6 and a low-pass filter 8; a second synchronous detector formed by an analog multiplier 7 and a low-pass filter 9; and two identical coils 14 and 15, forming a probe 18 remote from the remainder of the control system and connected thereto by two coaxial cables 12 and 13.

The probe 18 is placed on the surface of a metal part 17 which is to be tested. It is usually moved at a constant speed over this surface so as to sweep over it completely. The coils 14 and 15 are electromagnetically coupled to the part 17 and are coupled to each other, on account of their proximity. The coils carry two alternating currents, of squarewave form.

The magnetic fluxes of the two coils 14, 15 add or substract, depending on the senses of winding of the two coils and depending on the senses of the exciting currents in these coils. Both implementations are possible.

When a defect 16 is located opposite the coil 14, the eddy currents generated by the coil 14 do not have the same form as those generated by the coil 15, which translates into a difference between the impedances of the coils 14 and 15.

The excitation current of the coils 14 and 15 is provided by the output of the power amplifier 2, by way of the impedances 3 and 4, which form a Wheatstone bridge with the coils 14 and 15. A first end of the impedance 3 and a first end of the impedance 4 are connected to the output of the power amplifier 2. A first end of the coil 14 is connected to a reference potential of the control device by the screen of the cable 12. A first end of the coil 15 is connected to the reference potential of the control device by the screen of the cable 13. A second end of the coil 14 is connected to a second end of the impedance 3 by the center conductor of the cable 12. A second end of the coil 15 is connected to a second end of the impedance 4 by the center conductor of the cable 13. The second ends of the impedances 3 and 4 form the outputs of the Wheatstone bridge and are connected to an inverting input and a non-inverting input respectively of the differential amplifier 5. In addition, the second end of the impedance 3 is connected to an input-output terminal 23 of the generator 1, for a purpose described below.

Calculation shows that, for a sinusoidal signal, the output voltage of the bridge is a function of the difference between the complex impedances of the coils 14 and 15. The impedances 3 and 4 are each constituted by a pure resistance and an inductance in parallel, with values so chosen that the Wheatstone bridge has maximum sensitivity.

An input of the power amplifier 2 is connected to an output terminal 22 of the generator 1, which provides a squarewave. An output of the differential amplifier 5 is connected to a first input of the multiplier 6 and a first input of the multiplier 7. A second input of the multiplier 6 is connected to an output terminal 21 of the generator 1, which provides a first squarewave reference signal with the same frequency as the squarewave signal provided by the excitation output terminal 22.

The second input of the multiplier 7 is connected to an output terminal 24 of the generator 1, which provides a second reference signal 90° out of phase relative to the first reference signal. The outputs of the multipliers 6 and 7 are connected to the inputs respectively of a low-pass filter 8 and a low-pass filter 9. The outputs of the filters 8 and 9 are connected to two output terminals 10 and 11 respectively of the control device, providing two signals respectively representing the real part and the imaginary part of the difference between the complex impedances of the coils 14 and 15. These signals may be recorded on a chart recorder or may be processed by a digital computer, for example.

The Wheatstone bridge thus formed is fed by a squarewave signal and its output accordingly provides a squarewave signal, possibly distorted if the length of the cables 12 and 13 is great. The output signal of the Wheatstone bridge is amplified by the differential amplifier 5 and is then processed independently by the two synchronous detectors 6,8 and 7,9. Each of these synchronous detectors has the well-known property of only detecting a signal having a frequency and phase identical to those of the reference signal applied to the synchronous detector. As a result, each synchronous detector does not only eliminate parasitic signals induced in the probe 18 but also the harmonics resulting from the pulse form of the excitation signal. The low-pass filters 8 and 9 pass only very low frequencies that correspond to variations in the composition of the part 17 as its surface is swept over by the probe 18.

In a control device of conventional form, if the cables connecting the probe to the control device are very long, they both cause a reduction in sensitivity, because of the loss of a large proportion of the excitation power in the cables, and also cause poor operation of the synchronous detectors, because the reference signals no longer have a suitable phase in relation to the output signal of the Wheatstone bridge. Thus the excitation signal and the measurement signal are delayed by the length of the cables 12 and 13.

A solution to the problem of loss consists in removing the impedances 3, 4, the power amplifier 2 and the differential amplifier 5 to be as close as possible to the probe 18. The generator 1, the synchronous detectors 6,8 and 7,9 and the supply devices stay remote therefrom.

To overcome the problem of phase shift, the generator 1 comprises means for measuring the propagation time of a signal in the cables 12 and 13, passing from the generator 1 to the coils 14, 15 and back. These means provide a pulse on the terminal 23; this pulse propagates along the cable and then returns to the terminal 23. These means measure the round-trip time and derive a delay to be applied to each of the reference signals in order that the synchronous detectors shall operate in optimum manner.

Figure 2:
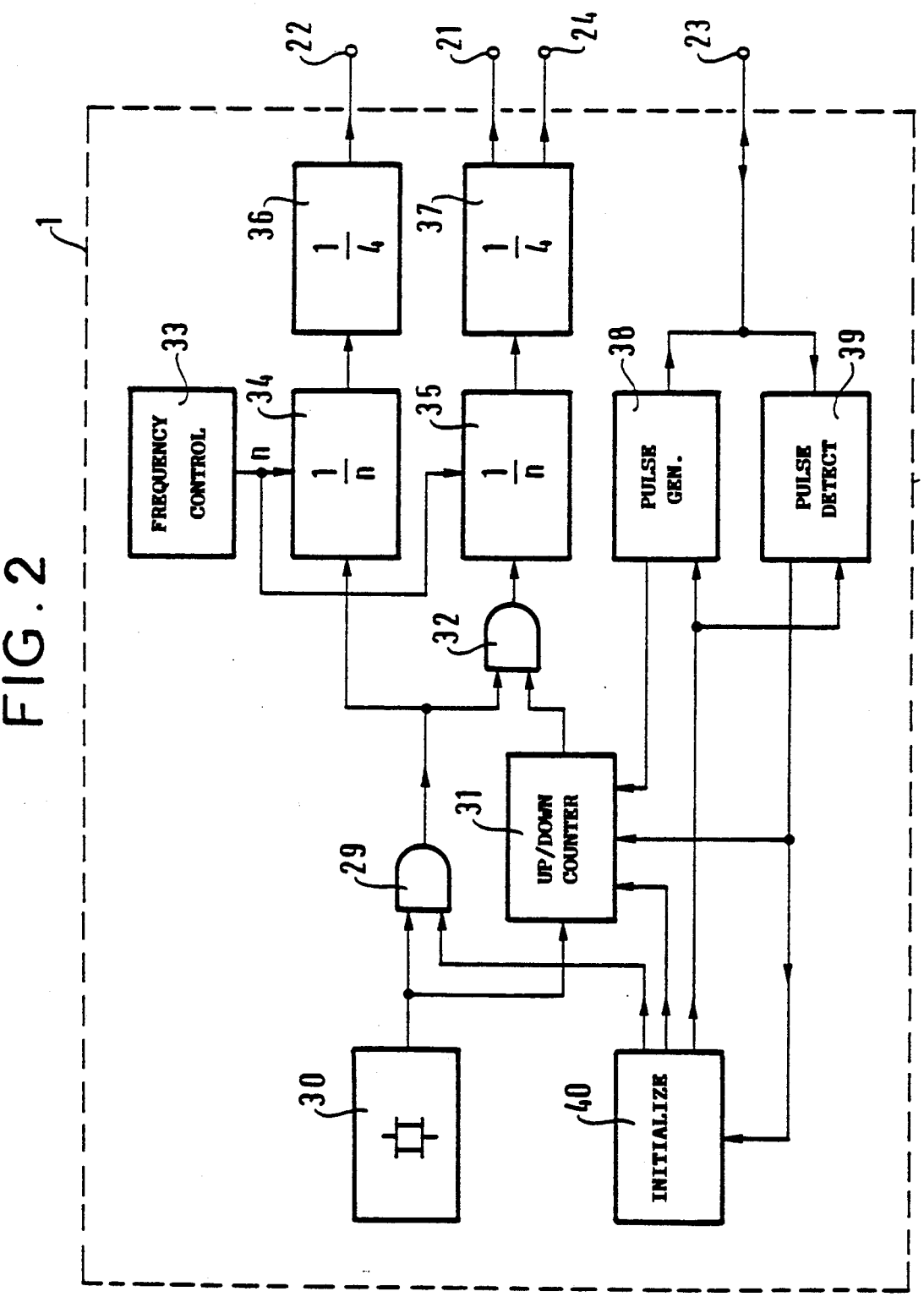
FIG. 2 is a general circuit diagram of the generator in this embodiment, in more detail.

FIG. 2 is a more detailed general block diagram of this embodiment. It comprises an oscillator 30 stabilized by a quartz crystal and outputting a pulse signal at a frequency of 128 MHz; an up-down counter 31 called the delay counter; two AND gates 29 and 32; a frequency control device 33; two programmable frequency dividers 34 and 35; two divide-by-four frequency dividers 36 and 37; a pulse generator 38; a pulse detector 39; and an initialization control device 40.

The output of the oscillator 30 is connected to one input of the AND gate 29 and to a clock input of the delay counter 31. A second input of the gate 29 is connected to a first output of the device 40. An output of the gate 29 is connected to a first input of the gate 32 and to a clock input of the divider 34. A second input of the gate 32 is connected to an output of the counter 31. An output of the gate 32 is connected to a clock input of the divider 35. A second output of the device 40 is connected to an enable input of the device 38 and to an enable input of the device 39. The device 38 has a first output connected to a count-enable input of the counter 31 and a second output connected to the input-output terminal 23. The device 39 has an output connected to an input of the device 40 and to a count-inhibit input of the counter 31, and has an input connected to the input-output terminal 23. A third output of the device 40 is connected to an up-down selection input of the counter 31.

The frequency of the signal provided by the oscillator 30 is divided by two frequency divider chains, one constituted by the dividers 34 and 36 and the other by the dividers 35 and 37.

The first chain provides the squarewave signal at the terminal 22, used after it has been amplified to energize the probe 18. The second chain provides the first reference signal at the output terminal 21, constituted by a squarewave signal of the same frequency as the energizing signal but phase-shifted by a delay which is a function of the length of the cables 12 and 13. It also provides the second reference signal at the output terminal 24, constituted by a squarewave signal with the same frequency as the energizing signal but having an additional phase shift of 90° relative to the first reference signal.

The dividers 34 and 35 each have a control input receiving a binary value determining the frequency division ratio n which it implements. This binary value is provided by an output of the device 33. This may be a manual control device or a digital computer automatically controlling the whole control device.

The programmable dividers 34 and 35 are of conventional form and can be constituted by a chain of commercially available integrated circuits, each programmable by a 4-bit binary value. The dividers 36 and 37 both effect division by a fixed value of 4 but they are arranged to provide three different signals at the output terminals 21, 22, 24. These three signals have the same frequency, which is $\frac{1}{4}n$ lower than the frequency of the oscillator 30.

The divider 37 has two outputs connected to the output terminals 21 and 24 and providing them with two respective signals out of phase by 90°. The divider 36 has only one output, connected to the output terminal 22, and which is in phase with the signal provided by the divider 37 at the terminal 21 in the situation in which the dividers 34 and 35 receive respective clock signals which are exactly the same.

The divider 34 has a clock input connected directly to the output of the AND gate 29 while the divider 35 has an input which is connected to this same output by way of the AND gate 32. The gate 32 is so controlled by an output of the delay counter 31 that the clock signal of the divider 35 is delayed by a certain number of periods relative to the clock signal applied to the input of the divider 34.

While preparing the generator 1, before testing a part, the delay counter 31 is preset with a value corresponding to the delay to be applied to the two reference signals provided by the output terminals 21, 24 respectively, relative to a signal provided by the output terminal 22.

The device 40 controls the steps in preparing the generator 1. For example, the device 40 may be a sequencer set in operation by manual actuation of a switch. The device 40 starts by initializing the counter 31 and the dividers 34 to 37, resetting these to zero. Then it selects the count-up mode of the counter 31. Then it enables the device 38 to transmit a pulse on the cable 12, and the device 39 to receive a return pulse. The device 38 commands the counter 31 to start to count at the instant when it sends a pulse to the terminal 23.

At the time of reception of the return pulse, the device 39 sends a signal to the counter 31 to stop the counting at a value which corresponds to the round-trip time of the pulse. The counter 31 stays preset to this value. The device 40 also receives the signal from the device 39 and it then sets the counter 31 to select the count-down mode. Then it enables the gate 29 to allow operation of the two frequency divider chains. The dividers 34 and 36 start to operate immediately. The counter 31 counts down the preset value and enables the gate 32 when it has counted down to zero. The dividers 35 and 37 then start to operate with a delay corresponding to the round-trip time of a pulse in the cables. When it has counted down to zero, the counter 31 stops. The gate 32 stays open. The control device is ready for control operations.

The scope of the invention is not limited to the embodiment described above. In particular it is open to the person skilled in the art to implement a control device with a single coil and a single synchronous detector. In this case, using a generator stabilized by a quartz crystal in combination with programmable frequency divider means leads to the same advantages as in the case of the control device with two coils and two synchronous detectors. The excitation signal is preferably a square-wave signal, since this is the form of signal produced most easily by means of conventional logic circuits, but the device according to the invention may also function with pulse signals having a mark-space ratio other than 1:1 and with periodic signals of any form.

I claim:

1. A non-destructive eddy current testing device, comprising:

supplying means for supplying a periodic power excitation signal;

at least one coil connected by a cable to an output of the supplying means and electromagnetically coupled to a part under test;

measuring means for detecting a change in an impedance of said coil, said measuring means including at least one synchronous detector for detecting a signal derived from said coil in accordance with a reference signal, with said supplying means including means for providing each synchronous detector with a respective reference signal; and said supplying means further includes means for measuring a propagation time of a signal passing from the supplying means to said coil and back again, and means for imposing on each said reference signal a delay equal to the measured propagation time, to thereby compensate for the effect of the length of said cable.

* * * * *